(12) United States Patent
Kaminski et al.

(10) Patent No.: US 11,037,671 B2
(45) Date of Patent: *Jun. 15, 2021

(54) DENTAL CHARTING SYSTEM

(71) Applicant: SOFTECH, INC., Farmington Hills, MI (US)

(72) Inventors: Raymond F. Kaminski, Bingham Farms, MI (US); Sherry Ann Dowling, Westland, MI (US); Eric J. Heverly, Novi, MI (US); Dimitris S. Papageorgiou, Ann Arbor, MI (US)

(73) Assignee: SOFTECH, INC., Farmington Hills, MI (US)

( * ) Notice: Subject to any disclaimer, the term of this patent is extended or adjusted under 35 U.S.C. 154(b) by 321 days.

This patent is subject to a terminal disclaimer.

(21) Appl. No.: 15/617,784

(22) Filed: Jun. 8, 2017

(65) Prior Publication Data

US 2018/0130558 A1 May 10, 2018

Related U.S. Application Data

(63) Continuation of application No. 12/616,845, filed on Nov. 12, 2009, now Pat. No. 9,710,603.

(60) Provisional application No. 61/113,822, filed on Nov. 12, 2008.

(51) Int. Cl.
*G16H 30/20* (2018.01)
*G16H 40/63* (2018.01)
*G16H 10/60* (2018.01)
*A61C 19/00* (2006.01)
*G06T 7/11* (2017.01)
*G16H 50/20* (2018.01)
*G06Q 40/08* (2012.01)
*G16H 15/00* (2018.01)

(52) U.S. Cl.
CPC ............. *G16H 30/20* (2018.01); *A61C 19/00* (2013.01); *G06T 7/11* (2017.01); *G16H 10/60* (2018.01); *G16H 40/63* (2018.01); *G16H 50/20* (2018.01); *G06Q 40/08* (2013.01); *G16H 15/00* (2018.01)

(58) Field of Classification Search
CPC ........ G16H 50/20; G16H 40/63; G16H 10/60; G16H 15/00; G06T 7/11; G06Q 50/24; G06Q 40/08; A61C 19/00; G06F 19/328
See application file for complete search history.

(56) References Cited

U.S. PATENT DOCUMENTS 7,343,305 B2 * 3/2008 Benn ...................... A61C 19/00
705/3
2009/0098504 A1 * 4/2009 Hourmand ........... A61C 19/043
433/72

* cited by examiner

*Primary Examiner* — Linh Giang Le
(74) *Attorney, Agent, or Firm* — Carlson, Gaskey & Olds, P.C.

(57) ABSTRACT

A computer-implemented dental charting system includes a computer storing tooth data for at least one patient and a display operable to display the tooth data. The computer is responsive to voice commands, and the display has a periodontal mode and a restorative mode. The display includes an exam overview window illustrating a plurality of tooth images, each tooth image corresponding to a patient tooth location, and an exam focus window. The exam focus window illustrates a magnified view of at least one of the plurality of tooth images, and illustrates data corresponding to the selected tooth location. The exam focus window may be displayed beside the exam overview window, as a floating window on top of the exam overview window, or on a physically separate display from the exam overview window.

7 Claims, 11 Drawing Sheets

FIG. 4

Set Pre-Existing Treatment Materials

| | Amalgam | Resin | Metallic | Gold | PFM | Porcelain | Acrylic | Sedative | Unknown | White Plastic | Gutta Percha | Silver Points | Paste | C-Clasp | T-Clasp | Precision |
|---|---|---|---|---|---|---|---|---|---|---|---|---|---|---|---|---|
| Restore | O | □ | □ | □ | □ | □ | □ | □ | □ | | | | | | | |
| Crown | □ | □ | □ | O | □ | □ | □ | □ | □ | | | | | | | |
| Onlay | | □ | □ | □ | □ | O | □ | □ | □ | | | | | | | |
| Inlay | | O | □ | □ | □ | □ | □ | □ | □ | | | | | | | |
| Bridge | | □ | □ | □ | □ | O | □ | | □ | | | | | | | |
| Maryland Bridge | | □ | □ | □ | □ | □ | O | | □ | | | | | | | |
| Cantilever Bridge | | □ | | □ | □ | □ | O | | | | | | | | | |
| Veneer | □ | □ | | | | O | | | | | | | | | | |
| Prefab Post | □ | O | | | | | | | | | | | | | | |
| Copings | | | O | | | | | | | | | | | | | |
| Root Canal | | | | | | | | | | □ | O | □ | □ | | | |
| Partial | | | | | | | | | | | | | | O | □ | □ |

TOOTH REVIEW ⌐□×

TOOTH REVIEW

TOOTH #2

153 ↙  154 ↙

156 ↙

| Date | Description | Type | Tx Status |
|---|---|---|---|
| 7/6/2009 | Apico | C | |
| 6/10/2008 | Clasp | C | |
| 6/10/2008 | Restore | PRE | Defective |
| 1/1/2009 | Denture | P | |
| 7/6/2009 | ANGLE | PRE | |
| 7/6/2009 | Impacted | PRE | |
| 6/10/2008 | Missing | PRE | |
| 1/20/2007 | Crown | T | Accepted |
| 6/10/2008 | EXT | T | Accepted |
| 6/10/2008 | implant | T | Accepted |
| 1/1/2009 | RCT | T | Accepted |
| 1/20/2007 | Restore | T | Accepted |

[ CLOSE ]

DENTAL CHARTING SYSTEM

The application claims priority to U.S. Provisional Application No. 61/113,822 which was filed on Nov. 12, 2008.

BACKGROUND OF THE INVENTION

This application relates to dentistry, and more specifically to periodontal and restorative dental charting.

Dentists and other dental professionals use dental charts to record information about their patients' teeth. This data may include periodontal information, such as a pocket depth of a recess between a patient's gums and tooth for a outer, facial side of the tooth and a inner, lingual side of the tooth. This data may also include restorative information about tooth conditions (e.g. cavities) and tooth treatments (e.g. fillings). Recording this data has required two people: a first person to take measurements or make observations, and a second person to record those measurements or observations.

SUMMARY OF THE INVENTION

A computer-implemented dental charting system includes a computer storing tooth data for at least one patient and a display operable to display the tooth data. The computer is responsive to voice commands, and the display has a periodontal mode and a restorative mode. The display includes an exam overview window illustrating a plurality of tooth images, each tooth image corresponding to a patient tooth location, and an exam focus window. The exam focus window illustrates a magnified view of at least one of the plurality of tooth images, and illustrates data corresponding to the selected tooth location. The exam focus window may be displayed beside the exam overview window, as a floating window on top of the exam overview window, or on a physically separate display from the exam overview window.

A method of presenting dental data stored on a computer-readable medium includes displaying on a first display portion an exam overview window including a plurality of tooth images, each tooth image corresponding to a patient tooth location. An exam focus window is displayed on a second display portion. The exam focus window includes a magnified view of at least one tooth image corresponding to a selected tooth location, and includes data corresponding to the selected tooth location. The exam overview window and the exam focus window have a periodontal mode and a restorative mode. A tooth review window illustrates a history for the selected tooth location. The history includes previous tooth conditions, suggested treatments, and a status of the suggested treatments. The tooth review window is selectively displayed on the first display portion in response to actuation of a tooth review command.

These and other features of the present invention can be best understood from the following specification and drawings, the following of which is a brief description.

BRIEF DESCRIPTION OF THE DRAWINGS

FIG. 4 illustrates another exam overview window configured to display periodontal examination data.

FIG. 7 illustrates a default materials configuration view.

FIG. 8 illustrates an example tooth review window.

FIG. 9*a* illustrates the example "treatment plan" view in a table view.

DETAILED DESCRIPTION OF THE PREFERRED EMBODIMENT

Figure 1:
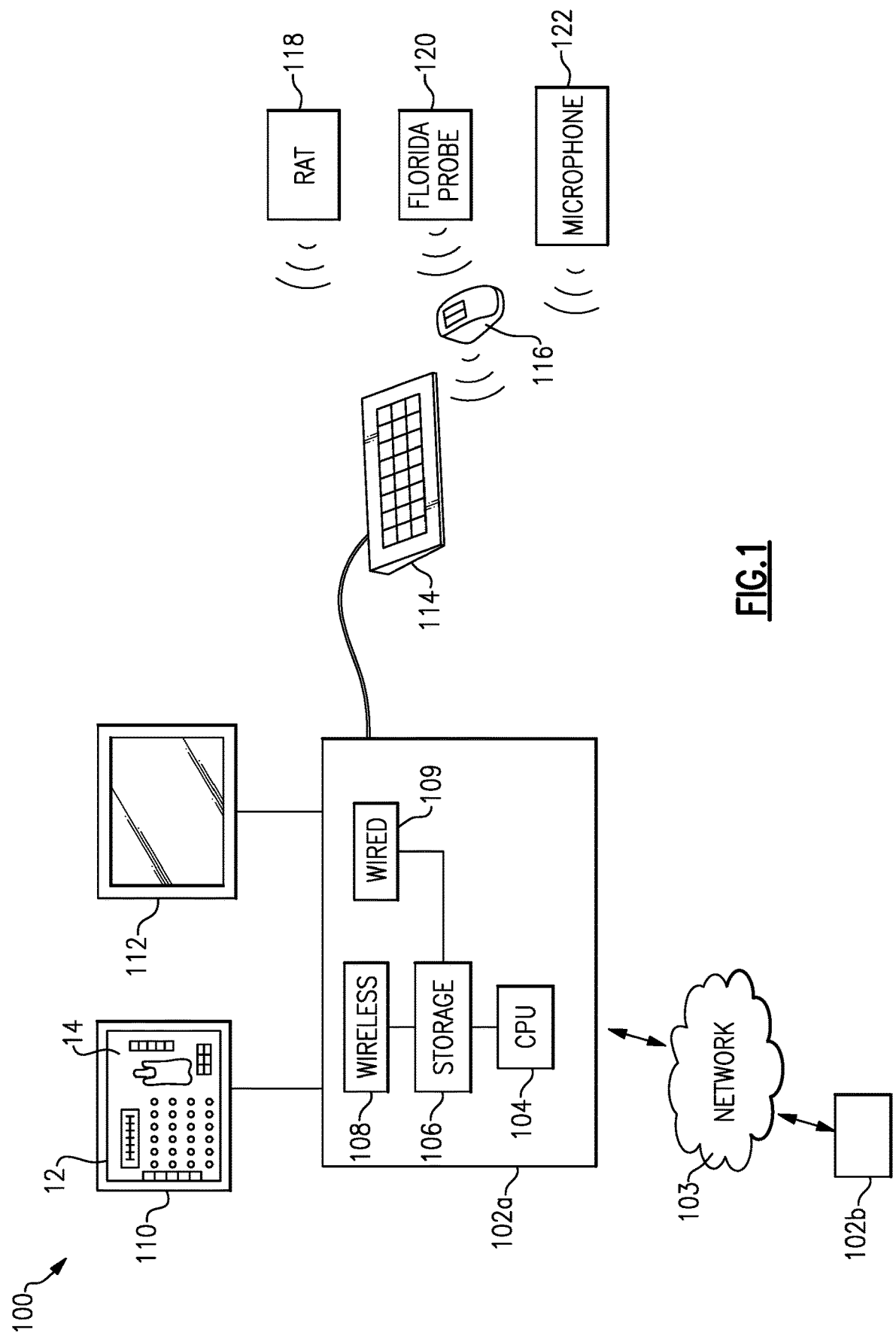
FIG. 1 schematically illustrates a periodontal charting system.

FIG. 1 schematically illustrates a dental charting system 100 for recording and retrieving periodontal and restorative data relating to teeth. The system 100 includes a computer 102*a*. The computer includes a CPU 104, a storage module 106, a wireless communication module 108, and a wired communication module 109. The storage module may include a hard drive, a flash drive, an optical drive, or any other storage medium. In one example the wireless module 108 corresponds to a wireless Ethernet card capable of communicating over WiFi, or a Bluetooth card. The computer 102*a* is connected to a first display 110 and an optional second display 112. The computer 102*a* communicates with the displays 110, 112 to illustrate an exam overview window 12 and an exam focus window 14 (see FIG. 2). In one example the system only includes the first display 110, and both of the windows 12, 14 are shown on the first display 110. In this example, the windows 12, 14 could be shown side-by-side, or the window 14 could be floating on top of the window 12. In one example, the system 100 shows the exam overview window 12 on the first display 110, and shows the exam focus window 14 on the second display 112.

In one example the system 100 includes a second computer 102*b* that communicates with the first computer 102*a* via a network 103. The network 103 may correspond to the Internet or another wide area network, or may correspond to a local area network, for example. The computers 102*a-b* may be configured in a client-server relationship such that computer 102*b* hosts a "data layer" and the computer 102*a* stores an "application layer" and a "graphical user interface" ("GUI") layer. The computers 102*a-b* may be configured in a "software as a service" ("Saas") relationship such that the computer 102*b* hosts a data layer and an application layer and the computer 102*a* stores an additional application layer for receiving voice commands and a presentation layer. The presentation layer may be implemented through a web browser, for example.

The system 100 (see FIG. 1) is responsive to a plurality of input modes, such as mouse 116, keyboard 114, Dental R.A.T. 118, Florida probe 120, and voice (via microphone 122). Of course, other input modes could be used. For example, the displays 110, 112 could be configured to be touchscreens responsive to touch commands. Certain entry modes, such as voice, enable a single user to take tooth measurements, and to efficiently record the measurements without requiring manual data entry through the mouse 116 or keyboard 114. Throughout this application, the term "user" is used to refer to an individual who would use the system 100, such as a dentist, a dental hygienist, etc., and the term "patient" is used to refer to an individual whose teeth are represented in the system 100.

The input devices 114-122 may communicate with the computer 102a via the wireless communication module 108 or the wired communication module 109. Although a plurality of the input devices 114-122 could be used to communicate with the computer 102a, it is understood that a single input device would suffice. It is also understood that a combination of these devices 114-122 can be used at the same time to enter data.

Figure 2:
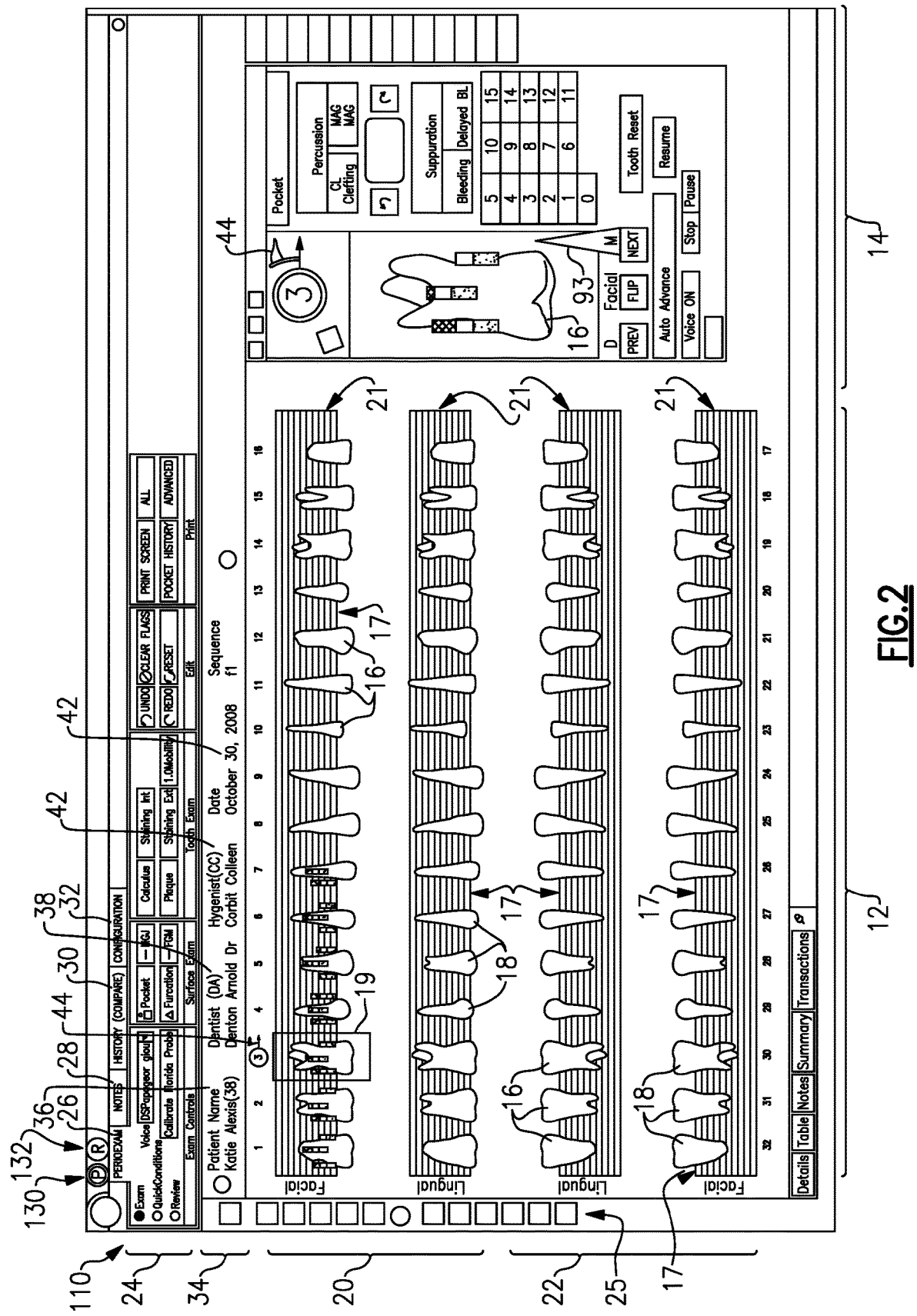
FIG. 2 illustrates an example exam overview window and an example exam focus window of the periodontal charting system of FIG. 1.

The system 100 has both a "periodontal" mode and a "restorative" mode. These modes may be toggled using periodontal button 130 or restorative button 132. FIG. 2 illustrates the windows 12, 14 of the system 100 in a side-by-side configuration in the periodontal mode. The exam overview window 12 includes a plurality of lingual tooth images 16 representing a lingual side of each of a patient's teeth, and a plurality of facial tooth images 18 representing a facial side of each of the patient's teeth. A first set 20 of facial and lingual tooth images corresponds to the patient's upper jaw, and a second set 22 of facial and lingual tooth images corresponds to the patient's lower jaw. Each tooth 16,18 is illustrated with respect to a gum line 17 and a ruler 21.

The exam overview window 12 includes a PerioExam tab 26, a Notes tab 28, a History/Compare tab 30, and a Configuration tab 32. Each of the tabs 26-32 correspond to different views in the exam overview window 12, and selecting a tab 26-32 activates a corresponding view. As shown in FIG. 2, the PerioExam tab 26 is active and the exam overview window 12 is in the PerioExam view. The PerioExam view includes a first toolbar 24 that offers the user a plurality of buttons and radio buttons to perform various functions, and a second toolbar 25 that offers additional options to the user. An administrative area 34 illustrates administrative data, such as a patient name 36, dentist name 38, hygienist name 40, date 42, etc. A selected tooth may be represented by a frame 19. The frame 19 may also be used to highlight several teeth at once (see FIG. 4). For example, a frame 19 could be used to indicate teeth that have deteriorated more than a predefined threshold. The exam focus window 14 illustrates the selected tooth. As described above, the exam focus window 14 could be illustrated on the first display 110 or the second display 112.

Various commands and features of the system 100 will now be described in detail.

Flag Command

The system 100 allows a user to flag a tooth to remind the user about a certain condition. In the example of FIG. 2, a user has flagged a third tooth 16, as indicated by the flags 44 in the exam overview window 12 and in the exam focus window 14. Different colors, shapes and styles may be used for the flags 44 to indicate various periodontal and restorative conditions, and to provide a reminder to a user between patient examinations.

The system 100 may display hints over a tooth. For example, if a user flagged a tooth three years ago for a specific condition, the hint above the flag 44 would indicate when the tooth was originally flagged, and unless the user removes the flag 44, the flag 44 will remain throughout the examination lifecycle for the specific patient. Also, the system 100 logs who set the flag, the date of the flag, the date the flag was cleared, etc.

The system 100 also allows users to print flags 44 on reports, and allows users to clear all flags 44. Flags 44 can also be captured as transactions to mark pre-existing and completed restorative conditions (e.g. implant, dentures, crowns) and clinical conditions (e.g. missing tooth, impacted), as will be described below in reference to the tooth review window 150 (see FIG. 8). The system 100 treats a flag 44 as a transaction that can be tracked through time.

Auto Advance/Resume

In the periodontal mode, the system 100 includes an "auto advance" function to automatically advance to successive teeth so that a user can speak measurements, and once all measurements for a teeth are recorded the system 100 automatically advances to the next tooth.

At times a user may want to override the auto advance function. For example, if certain comments or additional notes need to be made for a specific tooth, a user may wish to temporarily stop the auto advance in order to perform a task, such as having a side conversation with another user (e.g. a hygienist may wish to speak to a dentist). Also, it is possible that a user may need to make a note about a tooth out of sequence. For example, a user may be recording data about the seventh tooth when the second tooth starts bleeding. The user may wish to select the delayed bleeding button 50 for the second tooth (see FIG. 3). The user could say "Auto advance ON/OFF" (or another command to override the auto advance), say "Tooth two," say "delayed bleeding," and then say "resume." The system 100 could then say "seventh tooth" and the system 100 could resume recording data on the seventh tooth. In one example the system 100 resumes at the beginning of the seventh tooth. In another example the system 100 resumes on the measurement of the seventh tooth that was being recorded when the override occurred.

The resume command allows the user to return back to a tooth and exam that was selected at the time the auto advance override occurred. The resume command may be initiated by selecting the resume button 54 (see FIG. 3), or, for example, by speaking "resume." The resume command remembers not only an active tooth number at the time of interruption, but also remembers the specific exam that was administered at the time of override. This allows users to effectively start where they left off, saving time and increasing productivity.

History/Compare

Figure 4:
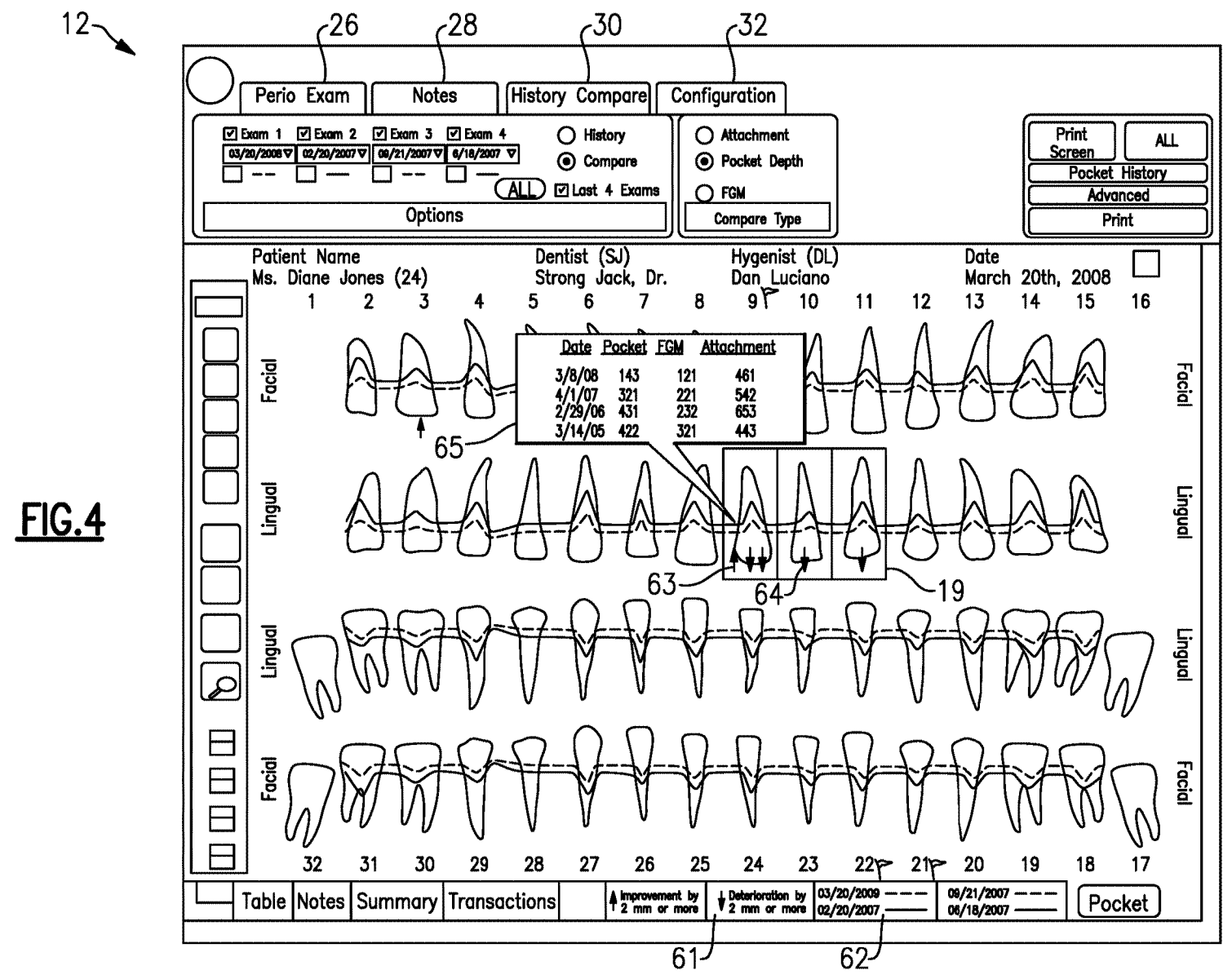

FIG. 4 illustrates the exam overview window 12 of the system 100 in the History/Compare view (note the History/Compare tab 30 is active) of the periodontal mode. The History/Compare view enables a user to instantly see what teeth are deteriorating or improving by comparing data from multiple exams using graphical indications.

Arrows may be used to indicate a gum improvement (e.g. arrow 63 from root of tooth 16 to gum line 17 to indicate depth reduction) or a gum deterioration (e.g. arrow 64 from gum line 17 to root of tooth 16 to indicate depth increase). In one example arrows are only used if the improvement or deterioration exceeds a predetermined threshold (such as two units). The predetermined threshold may be adjusted on an administrative or per-user level (as described in the Configuration section below). Different colors may be used for the arrows, such as a green arrow for an improvement and a red arrow for deterioration. Of course, other colors could be used. The arrows are explained in a first legend 61. A second legend 62 indicates symbols used to indicate various examinations. In the example of FIG. 4 lines having different weights or styles (e.g. solid, dashed, etc.) are used in the second legend 62 to indicate various previous examinations. However, color could also be used to distinguish the different indicators.

A comparison window 65 may be used to provide the various measurements corresponding to the multiple exams. In one example, the comparison window 64 is activated by hovering over the selected teeth (upper jaw lingual teeth nine, ten, and eleven in FIG. 4) and hovering over them with a pointer. Although the comparison window 64 of FIG. 4 illustrates data from four previous tests, it is understood that more or less data could be shown in the window 65. Also, although pocket depth, FGM, and attachment data is shown, it is understood that different data could be shown in the window 65. In one example the comparison window 35 could be shown as a separate window floating on top of the window 12.

Configuration

The system 100 provides extended configuration at administrative user ("admin") level and at the non-administrative user ("non-admin") level in both the periodontal and restorative modes. One way to enter configuration preferences is to select the configuration tab 32 (see FIG. 2). Some example configurable features include a preferred sequence of teeth to use for the auto advance feature, the predetermined threshold associated with the gum improvement and deterioration arrows 63, 64, and report templates. An admin user can choose to either permit or prevent non-admin users from overriding the admin user's predefined settings.

Also, as will be described below in connection with FIG. 6, default materials may be selected in the restorative mode as a configuration feature.

Exam Focus Window: Periodontal Mode

Figure 3:
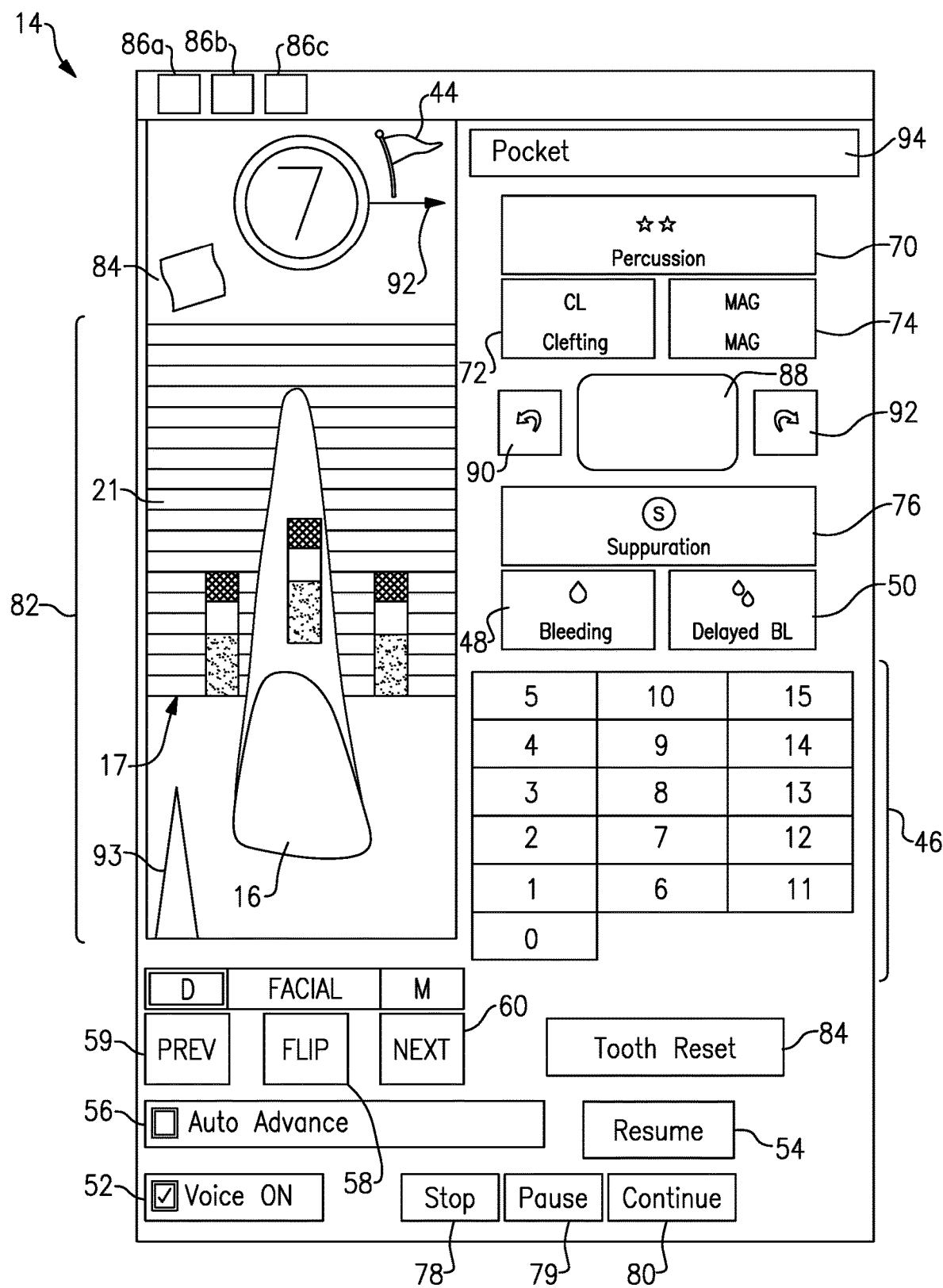
FIG. 3 illustrates another example exam focus window.

FIG. 3 illustrates an example exam focus window 14 in the periodontal mode. The exam focus window 14 is a dedicated window that provides detailed information about an active tooth. For example, in the example of FIG. 3 the upper jaw seventh tooth is active.

The exam focus window includes a plurality of options in the periodontal mode. A user may select any of a plurality of depths 46. A bleeding button 48 may be used to indicate bleeding of a tooth 16, 18. A delayed bleeding button 50 may be used to indicate delayed bleeding of a tooth 16, 18. A voice activation button 52 may be selected to turn voice control ON of OFF. The auto advance checkbox 56 may be selected to toggle the auto advance feature ON or OFF. Also the flip button 58 may be used, as will be described below.

The exam focus window 14 can be sized and moved by a user as desired, and although the exam overview window 12 and the exam focus window 14 are illustrated side-by-side on the first display 110 in FIG. 2, different viewing configurations would be possible. For example, the exam focus window 14 could be a floating window that is displayed on top of the exam overview window 12. Also, the exam overview window 12 could be shown on the first display 110 and the exam focus window 14 could be shown on the second display 112. In one example the exam focus window 14 is illustrated on the second display 112, and the second display 112 is a widescreen display that may be rotated to have a portrait as opposed to a landscape orientation. In one example the displays 110, 112 are visible from a distance (e.g. 5-6 feet away), and provide visual feedback to a user using the system 100, such that the user can be taking measurements and interacting with the system 100 at a distance.

The exam focus window 14 includes display style buttons 86a-c that may be selected to change how the exam focus window 14 is displayed.

Flip Command

The Flip command enables a user to switch between lingual and facial side of a tooth with a single command. This command may be entered either vocally (e.g. saying "Flip") or by clicking the Flip button 58.

One method of conducting a periodontal exam is to follow a sequence by taking measurements for a first side (facial or lingual) of a first tooth, proceeding to a next tooth in the sequence, taking measurements for the first side of that next tooth, and so on. A measurement of the second side of the first tooth is not taken until the sequence returns to the first tooth. However, some users may desire to take measurements for both sides of the first tooth before proceeding. Such a user may use the Flip command to achieve this by taking measurements for a first side of the first tooth, speaking "Flip" (or clicking the Flip button 58), taking measurements for the second side of the first tooth, speaking "Flip" (or clicking the button 58) and then proceeding to the next tooth. The system 100 is therefore able to accommodate a wide variety of examination preferences.

Voice Triplet Command

The voice triplet feature allows a user to provide multiple commands or measurements in a single spoken entry. For example when taking measurements in the periodontal mode, instead of a user saying "two" and waiting to hear audio feedback, saying "one" and waiting for audio feedback, and then saying "two" and waiting for audio feedback, the user could simply say "two one two" and the system 100 would parse those measurements simultaneously and repeat back "two one two" to the user. This enables a user to quickly record three pocket depths for one full side of a tooth. The system 100 is operable to process the words "two one two" as a single entry in a voice recognition dictionary, as opposed to the method described above of speaking a first measurement, receiving feedback, speaking a second measurement, receiving feedback, etc., which would be processed as multiple entries in the voice recognition dictionary. Thus, entry speeds can be improved on the order of three times. The voice triplet feature is also applicable to other exam types, including Free Gingival Margin ("FGM") and Muco-Gingival Junction ("MGJ"), etc.

The voice triplet command feature provides an opportunity for reducing the duration of a periodontal exam. For example, when entering data using a keyboard, a data entry speed may be between 70-90 tests/numbers per minute as compared to 30-40 tests/numbers per minute for voice commands. With this feature, the voice command speed may be between 80-110 tests/numbers per minute, making voice entry as fast as, if not faster than, the keyboard entry.

Feedback

The system 100 is operable to provide feedback in response to voice commands. As described above, in the periodontal mode a user could record measurements by speaking, for example, "two three two" and the system 100 could repeat back to the user "two three two" to confirm that the measurements were correctly received. The feedback speed could be altered to provide feedback as quickly or as long as desired. For example, a user could configure the system 100 to accept 30 measurements per minute. The feedback provides immediate validation to all modes of entry, and helps prevent data entry errors prevalent in the prior art.

Sample Voice Commands

The following is a sample series of voice commands in the periodontal mode: "Auto Advance ON, Pocket, 2, 1, 2, Flip, 2, 3, 1, Flip, FGM." This series of commands would turn ON the auto advance feature (see button 56), would indicate a pocket examination (see exam type selector 94), would indicate measurements "2 1 2" for a first side of a tooth, and would indicate would flip the tooth, and would then indicate measurements "2 3 1" for a second side of the tooth. The FGM type examination would then be selected.

Other Periodontal Features

The exam focus window 14 includes a plurality of other options and features that will now be described. Referring to FIG. 3, the percussion button 70, the clefting button 72, the MAG button 74, and the suppuration button 76 may be used to indicate percussion, clefting, MAG, or suppuration of a tooth.

The tooth reset button 84 resets all measurements for a tooth so that a user may provide a new set of measurements or clear an erroneous set of measurements. The stop button 78, pause button 79, and continue button 80 may be used to interrupt a session, or to continue the session. The previous button 59 and next button 60 may be used to advance to a consecutive or previous tooth. The tooth display area 82 illustrates a magnified active tooth 16 and gum line 17. The note button 84 may be actuated if a user wants to make a note about an active tooth. A directional arrow 92 may be used to indicate a direction of the sequence (i.e. which tooth is to be measured next). A marker 93 may be used to indicate which of the three measurements on the tooth is the current measurement (i.e. the measurement currently being recorded). In the example of FIG. 2, the marker 93 indicates that the third measurement is the current measurement. In the example of FIG. 3, the marker 93 indicates that the first measurement is the current measurement.

A visual numeric feedback display 88 visually indicates a recorded measurement or plurality of measurements of the active tooth. Tooth rotation buttons 90, 92 may be used to indicate that a tooth is angled (which can affect depth measurements). If a user rotates a tooth using the buttons 90, 92, the rotation would also be shown in the exam overview window 12. A user can also indicate if a tooth is impacted using the user interface. If a user indicated that a tooth was impacted, the tooth would be illustrated as impacted in both the exam overview window 12 and the exam focus window 14. In one example, if a user designates a tooth as impacted that tooth is omitted from the auto advance sequence, as no depth measurements can be made for an impacted tooth. A user could also zoom, pan, or move a tooth. For example, a user could click and drag a tooth to move the tooth in either the exam overview window 12 or the exam focus window 14. Also, a user could magnify a tooth, and then click and drag the tooth to pan the tooth in the magnified view. An exam type selector 94 may be used to choose different types of examinations.

As discussed above, the frame 19 is a border around a tooth 16, 18 that enables the user to quickly locate the tooth. The frame 19 helps to avoid misnumbering (e.g. a user is less likely to be mistaken about what tooth is active). The frame 19 is particularly useful when a user is not particularly close to the display 110, 112 and when a patient has teeth are moved and/or rotated.

Users have the ability to turn ON or OFF the gum line 17, the ruler 21, and the frame 19. Users also have the ability to print any screen and save it as a PDF report.

The system 100 provides key reports and associated structure and ability to select any combination to print or save, including reports with the PSR score.

Restorative Mode

As discussed above, the system 100 has both a periodontal mode and a restorative mode, and these modes may be toggled by selecting buttons 130, 132 (see, e.g., FIG. 2). In the restorative mode a user may enter data regarding tooth treatments (e.g., root canals, bridges, dentures, etc.) and conditions (e.g., missing teeth, impacted teeth, cracked teeth, etc.) Various features of the restorative mode will now be discussed.

Restorative Mode Features

Figure 5:
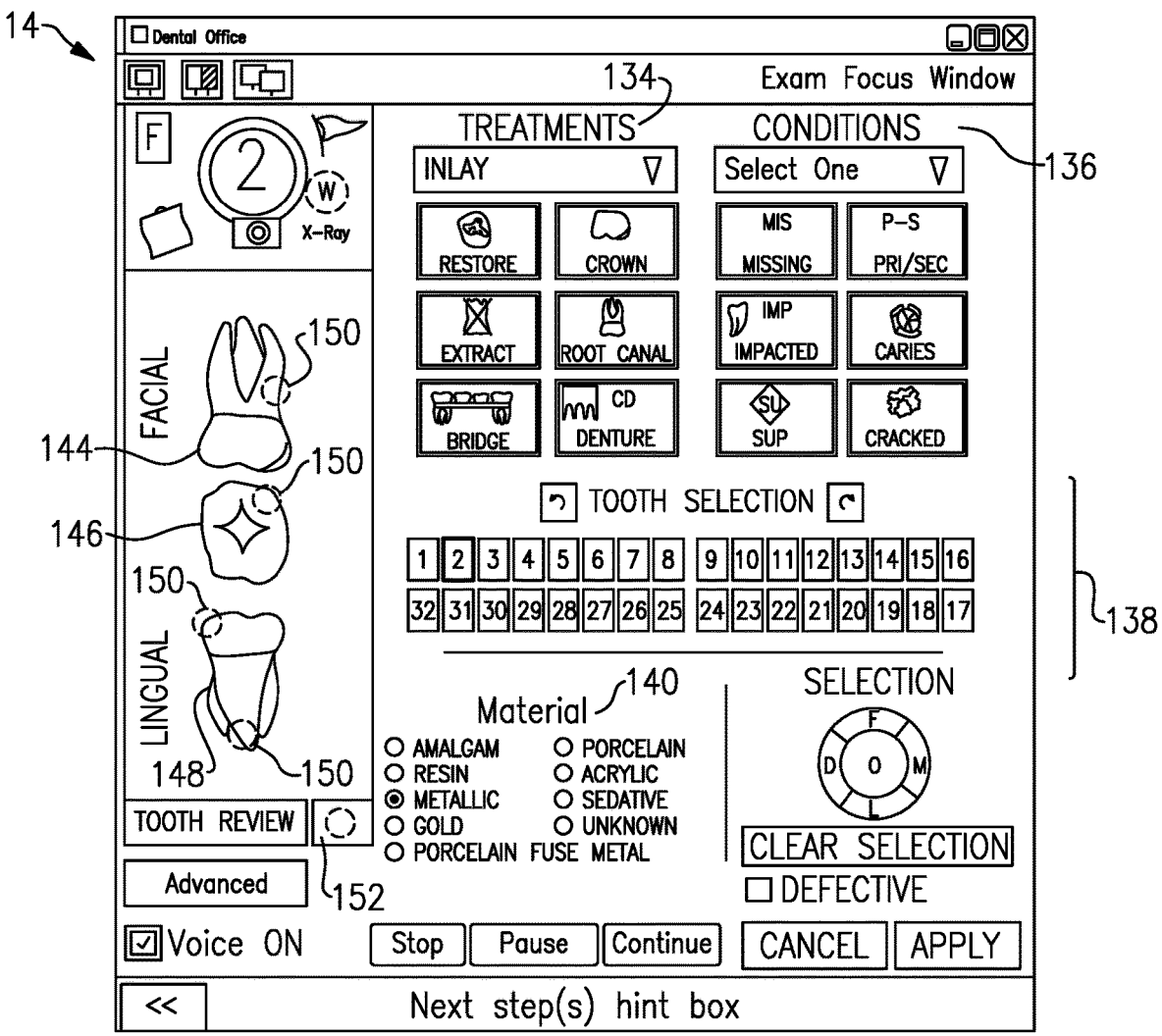
FIG. 5 illustrates an example exam focus window in the restorative mode.

Referring to FIG. 5, in the restorative mode, areas of concern may be indicated using a marker 150. Thus, if a user is concerned about a particular area of a tooth and wants that area to be monitored, button 152 can be selected to create a tooth watch marker 150.

Figure 6:
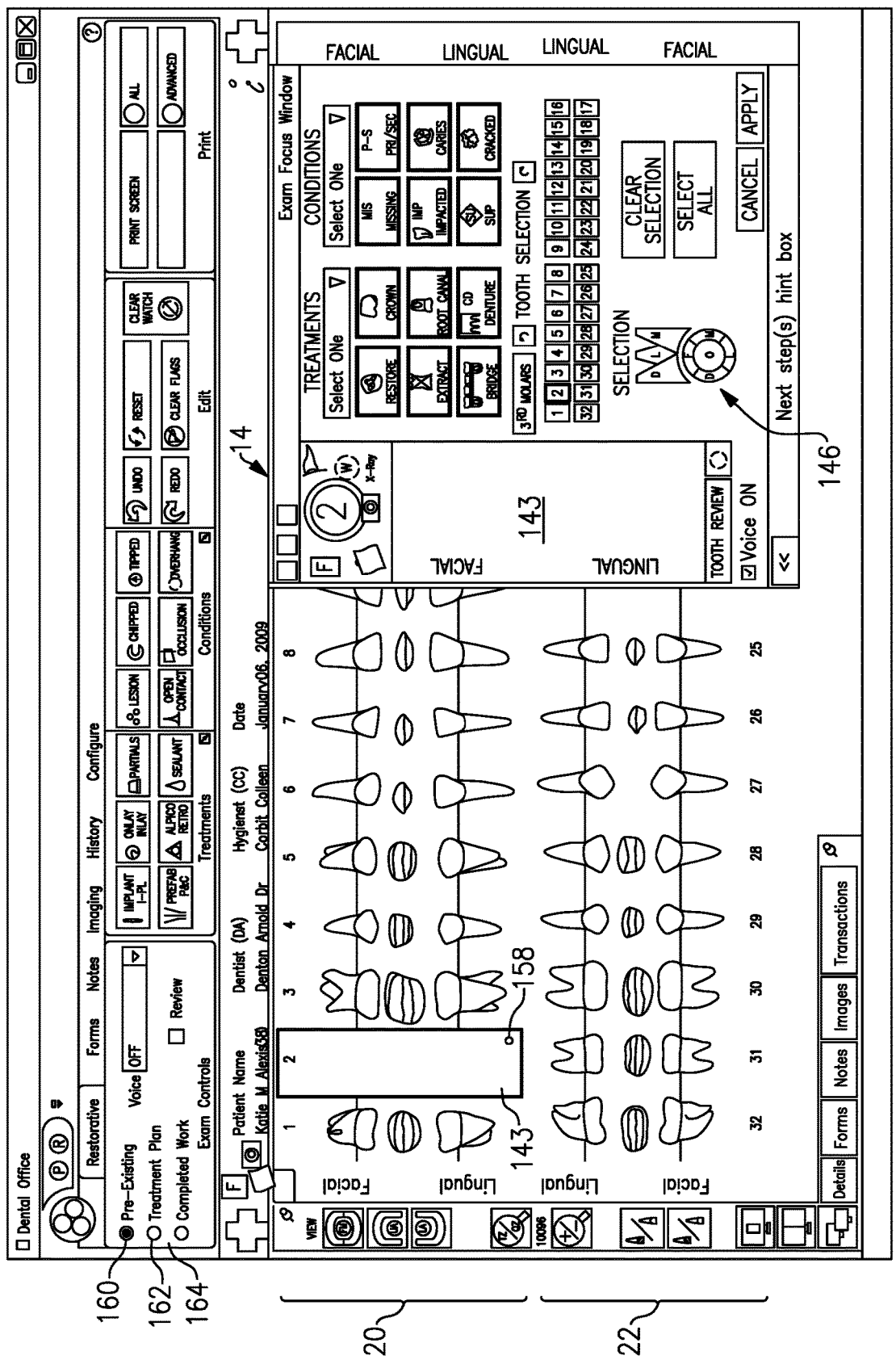
FIG. 6 illustrates another example of the exam overview window and exam focus window in the restorative mode.

FIG. 6 illustrates examples of the windows 12, 14 in the restorative mode. As shown in FIG. 6, if a missing tooth 143 in the window 12 may be shown as a missing tooth 143 in the exam focus window 14.

FIG. 6 also illustrates a root selector 146. In the restorative mode, it may be necessary to indicate a relevant root of a tooth. For example, if a dentist performs a root canal, it would be desirable to indicate which root of a tooth was operated on. The root selector 146 enables a user to perform such an indication. In one example the root selector 146 dynamically changes in response to which tooth is actively selected.

In response to a single-rooted tooth, the root selector 146 indicates only an "R" for root. In response to a two-rooted tooth, the root selector 146 indicates either L and F buttons (for a tooth having a lingual/facial orientation), or M and D buttons (for a tooth having a mesial/distal orientation). In response to a three-rooted tooth, the root selector 146 indicates M and D and L buttons (for mesial, distal, lingual).

As shown in FIG. 6, a user may select buttons 160, 162, 164 to switch between a "pre-existing" view in which pre-existing teeth treatments can be viewed, a "treatment plan" view in which proposed treatments can be viewed, and "completed work" view in which completed procedures can be viewed. The "pre-existing" view may be used to reflect patient tooth information as it exists when the patient sits in the dental chair. That is, this view may include work performed in previous dental visits to a dentist using the system 100 or to previous visits to other unknown dentists.

Exam Focus Window: Restorative Mode

Referring again to FIG. 5, the exam focus window 14 is illustrated in the restorative mode. In this mode a plurality of treatments 134 (e.g., restore, crown, extract, root canal, bridge, etc.) and a plurality of conditions 136 (e.g., missing, impacted, cracked, etc.) can be selected. A tooth selector 138 may be used to select an active tooth. A tooth material selector 140 may be used to select a material. For example, if a dentist was creating a filling the material of the filling could be indicated.

Default materials may be entered in a material selection window 142 (see FIG. 7). This can save considerable time for a user of the system 100. For example, if a user was entering a crown, the system 100 could lookup the default crown material and enter that material without requiring a user to select the material during entry. This could save time if the user was entering data using voice commands. For example, if a default crown material was gold, a user could enter a crown on tooth 3 by simply saying "crown, tooth 2, tooth 4" and the system would automatically know that gold was being used. This is in contrast to the prior art where a user would have to manually enter the crown by using a mouse to click "crown, tooth 2, gold, tooth 3, gold, tooth 4, gold."

As shown in FIG. 5, the exam focus window 14 in the restorative view includes a plurality of magnified tooth images: a facial tooth image 144, an occlusal tooth image 146, and a lingual tooth image 148

Tooth Review

FIG. 8 illustrates an example tooth review window 150. The tooth review window 150 displays a restorative mode history for a selected tooth location. The history includes previous tooth conditions 153, suggested treatments and a status of the suggested treatments 154. The tooth review window also indicates dates 156 of previous conditions. In one example the tooth review window 150 is actuated in response to selecting a button 158 in proximity to an active tooth (see FIG. 6). The tooth review window enables a user to quickly obtain a history for a specific tooth. This feature is quite helpful, as it avoids the need for a user to parse through data for all teeth when only a single tooth is of concern.

Treatment and Insurance Plans

Figure 9:
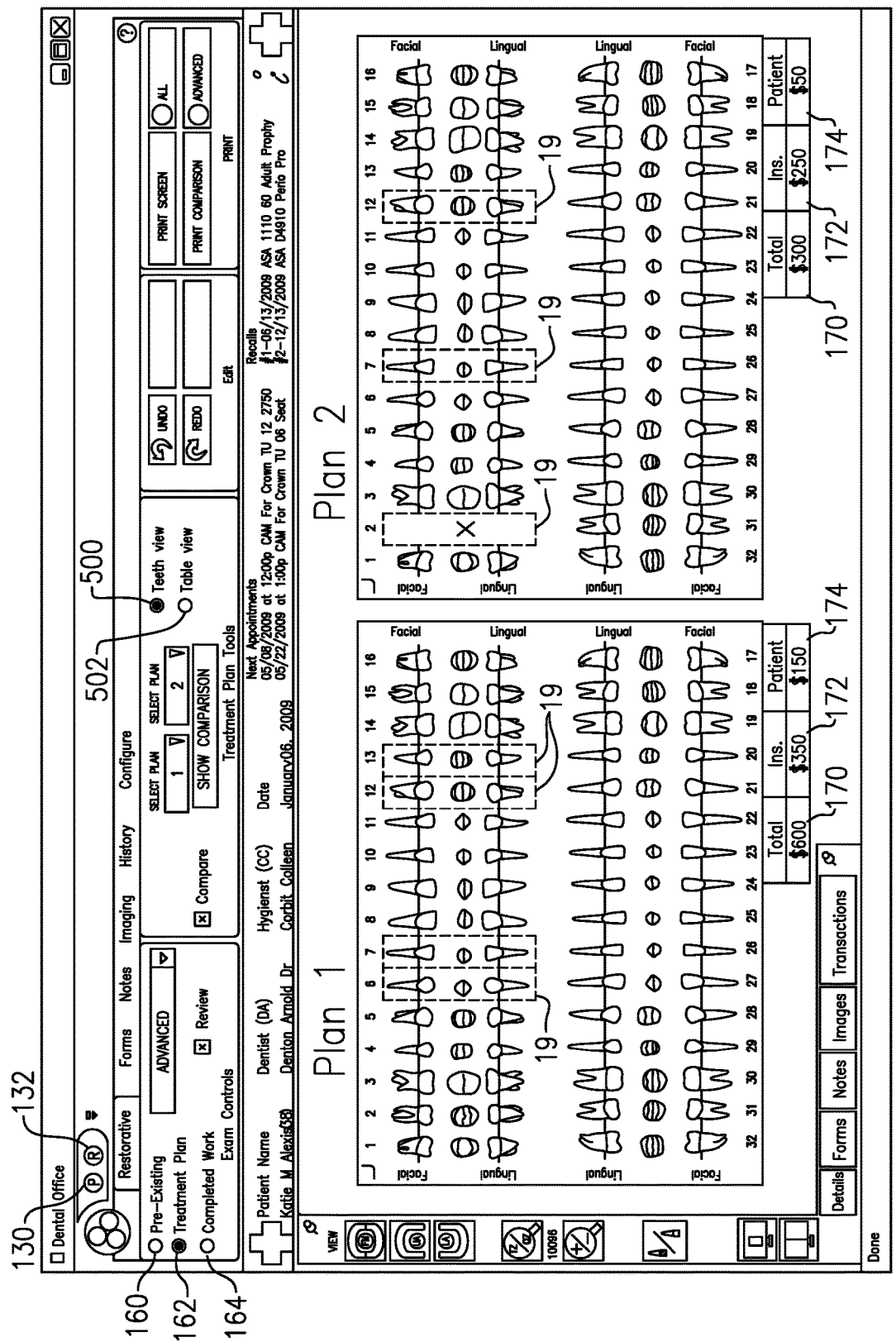
FIG. 9 illustrates an example "treatment plan" view in a teeth view.

FIG. 9 illustrates an example "treatment plan" view (note that button 162 is selected) in the restorative mode. In this view, a first portion 166 of the exam overview window 12 illustrates a first proposed treatment, and a second portion 168 of the exam overview window 12 illustrates at least one of a second proposed treatment or existing conditions. A frame 19 having a dotted line border may be used to indicate teeth which have proposed or planned procedures.

The treatment plan view may be used to discuss potential and performed treatments with a patient, and to help a patient understand the costs associated with a treatment. Each portion 166, 168 includes a total cost 170, an insurance cost 172, and a patient out-of-pocket cost 174. As shown in FIG. 7, a dentist is recommending that a patient perform work on teeth 6-7 and 12-13 in a first plan (see portion 166) and is recommending that the patient have tooth 2 removed and have work performed on teeth 7 and 12 in a second plan (see portion 168). In one example, when a user enters a proposed treatment the user enters a predefined treatment code that can be submitted to an insurance company or an insurance database to determine an insurance coverage amount. In this example, codes put forth by the American Dental Association ("ADA") or equivalent codes may be used.

Figure 9A:
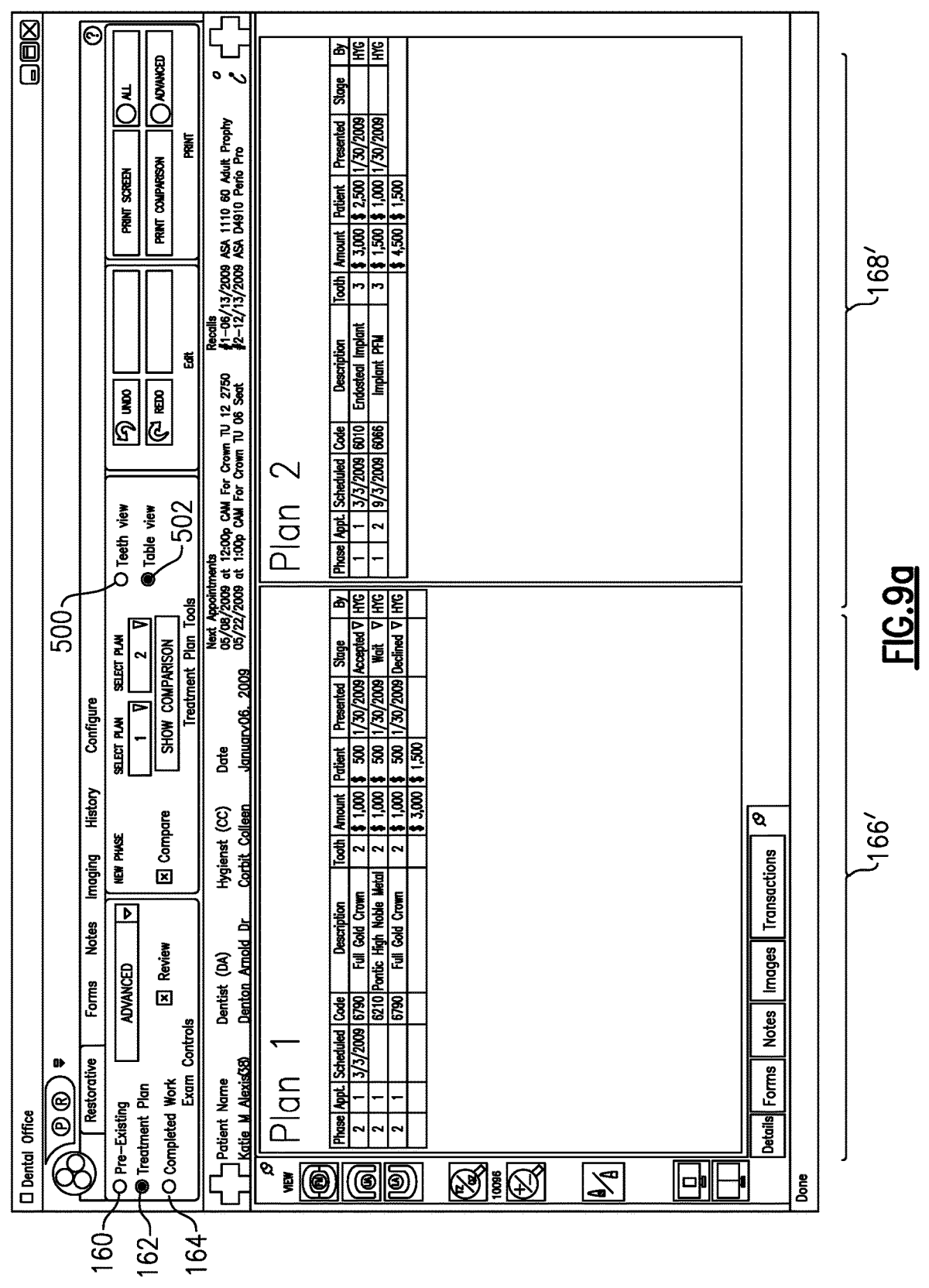

Within the treatment plan view, a user may select between a "teeth view" 500 (see FIG. 9) or a "table view" 502 (see FIG. 9a). The teeth view, as shown in FIG. 9, graphically illustrates treatment information using tooth images. The table view, as shown in FIG. 9a, illustrates treatment information using one or more tables.

Figure 10B:
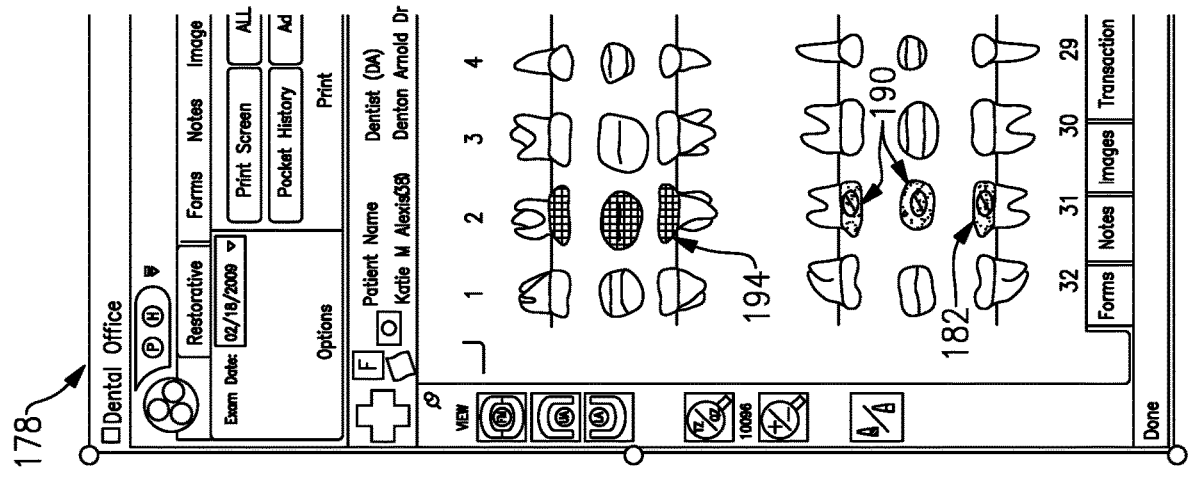
FIG. 10*b* illustrates an example "tooth treatment history" view in the restorative mode.
Figure 10A:
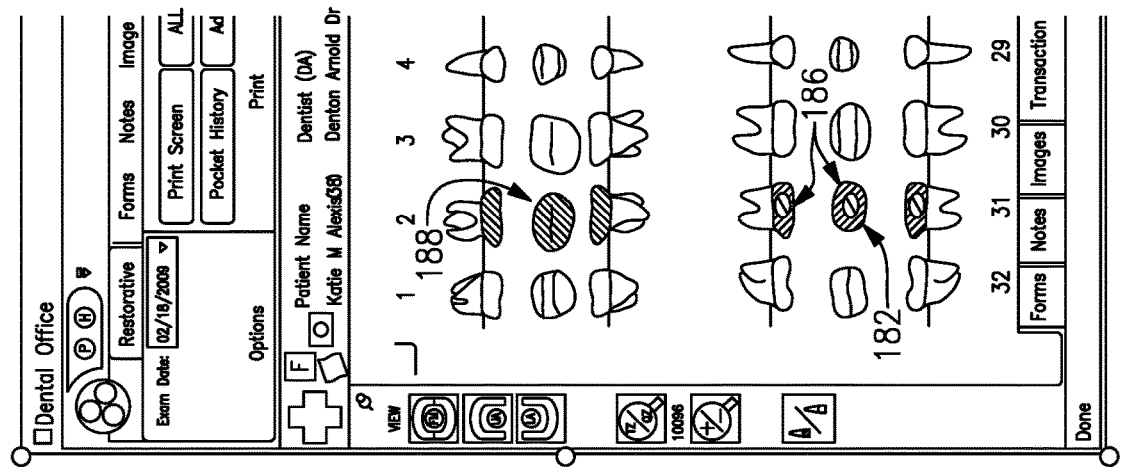
FIG. 10*a* illustrates an example "natural tooth" view in the restorative mode.

FIG. 10a illustrates a natural tooth view 176, and FIG. 10b illustrates a tooth treatment history view 178, each of which could be viewable in the "pre-existing" or "completed work" views (see buttons 160, 164). The natural tooth view 176 uses tooth images to indicate what a tooth looks like. For example, the shading 186 on tooth 31 indicates that an amalgam filling has been created. The shading 188 on tooth 2 indicates that a gold filling has been created. Of course, instead of shading 186 a grey coloring could be used and instead of shading 188 a gold coloring could be used. The tooth treatment history view 178 using a first shading 190 to indicate procedures performed by a current dentist and uses a second shading 184 to indicate procedures performed by a previous dentist. Of course, coloring could be used in conjunction with or instead of shading. This feature could be useful for certain procedures, such as crowns, which many dentists warrant will last for a number of years (e.g. 5 years). If the procedure was performed by a previous dentist, a current dentist would not be obligated to fix the tooth for free, for example.

FIG. 10b illustrates an example completed work view 178 which illustrates work performed on a patient's teeth. The shading on 190 on tooth 31 illustrates that an external treatment has been performed. Symbol 182 indicates a defective condition on a tooth. The shading 194 on tooth 2 indicates that an internal treatment has been performed. Of course, instead of or to supplement the shading 190, 194, color could be used.

Zooming and Panning

A user may zoom or pan within the exam overview window 12 if desired. In one example, if the user zooms in the exam overview window 12 and then selects a tooth in the exam focus window 14, the exam overview window 12 will maintain a zoom level and will pan or scroll to the selected tooth such that the selected tooth may be viewed simultaneously in both windows 12, 14.

Scalability

The system 100 is scalable, and may be expanded to include multiple machines operating across a wide area network. For example, a doctor could create a proposed treatment on a first computer (e.g., in the doctor's office or home). The doctor could then present the treatment on a first computer in a dental office. An administrative assistant could then transmit treatment information to an insurance company on a second computer in the dental office. Of course this configuration is only exemplary, and it is understood that other configurations would be possible.

Although many features of the system 100 have been described in the context of a button that may be selected, it is understood that these features and options could be activated by any of the aforementioned input modes, including, but not limited to, mouse, keyboard, Dental R.A.T., Florida probe, and voice.

Although a preferred embodiment of this invention has been disclosed, a worker of ordinary skill in this art would recognize that certain modifications would come within the scope of this invention. For that reason, the following claims should be studied to determine the true scope and content of this invention.

What is claimed is:

1. A computer-implemented dental charting system comprising:
  a computer storing tooth data for a plurality of teeth for a patient, the computer being responsive to voice commands to receive periodontal measurements sequentially for each of the plurality of teeth and to associate the periodontal measurements with each of the plurality of teeth, wherein each of the plurality of teeth is sequentially a "selected tooth" for which the computer is receiving periodontal measurements, wherein the computer is programmed to receive three consecutively-spoken periodontal measurements without requiring a speaker to pause between spoken measurements, to store the three consecutively-spoken periodontal measurements, to parse the three consecutively-spoken periodontal measurements, and to associate the three periodontal measurements with the selected tooth; and
  a display operable to display the tooth data.

2. The computer-implemented dental charting system of claim 1 wherein the computer is further programmed to repeat the three periodontal measurements as audio feedback.

3. The computer-implemented dental charting system of claim 2 wherein the computer is programmed to receive the three consecutively-spoken periodontal measurements without providing audible feedback between the three consecutively-spoken periodontal measurements, and to repeat the three periodontal measurements as audio feedback after storing the three consecutively-spoken periodontal measurements.

4. A method of storing dental data on a computer-readable medium including the steps of:
   a) receiving on a computer three consecutively-spoken periodontal measurements without requiring a speaker to pause between spoken measurements;
   b) storing the three consecutively-spoken periodontal measurements on the computer; and
   c) parsing the three consecutively-spoken periodontal measurements on the computer and associating the three periodontal measurements with a tooth of a patient.

5. The method of claim 4 further including the steps of:
   d) after said step c), automatically repeating said steps a)-c) for an adjacent tooth of the patient.

6. The method of claim 5 further including the steps of:
   e) after said step c), repeating the three periodontal measurements as audio feedback.

7. The method of claim 6 wherein the computer receives the three consecutively-spoken periodontal measurements without providing audible feedback between the three consecutively-spoken periodontal measurements, the method further including the step of repeating the three periodontal measurements as audio feedback after said step b).

* * * * *